(12) United States Patent
Stevick et al.

(10) Patent No.: US 7,961,912 B2
(45) Date of Patent: Jun. 14, 2011

(54) METHOD AND APPARATUS FOR DYNAMIC SPACE-TIME IMAGING SYSTEM

(76) Inventors: Glen R. Stevick, Berkeley, CA (US); David M. Rondinone, Berkeley, CA (US); Jerome R. Singer, Berkeley, CA (US); Allan L. Sagle, Berkeley, CA (US)

( * ) Notice: Subject to any disclaimer, the term of this patent is extended or adjusted under 35 U.S.C. 154(b) by 1040 days.

(21) Appl. No.: 11/811,239

(22) Filed: Jun. 8, 2007

(65) Prior Publication Data

US 2007/0299338 A1    Dec. 27, 2007

Related U.S. Application Data

(63) Continuation-in-part of application No. 10/966,095, filed on Oct. 14, 2004, now Pat. No. 7,620,209.

(51) Int. Cl.
*G06K 9/00* (2006.01)
(52) U.S. Cl. .................................. 382/106; 382/154
(58) Field of Classification Search .......... 382/106–108, 382/142–154
See application file for complete search history.

(56) References Cited

U.S. PATENT DOCUMENTS

| 6,754,370 B1* | 6/2004 | Hall-Holt et al. | 382/106 |
| 6,965,690 B2* | 11/2005 | Matsumoto | 382/154 |
| 7,620,209 B2* | 11/2009 | Stevick et al. | 382/106 |
| 2005/0068544 A1* | 3/2005 | Doemens et al. | 356/601 |

* cited by examiner

*Primary Examiner* — Manav Seth
(74) *Attorney, Agent, or Firm* — Howard Cohen

(57) ABSTRACT

A method for creating a 3D map of the surface contours of an object includes projecting a variety of patterns onto the object, and imaging the patterns as they fall on the object to encode the topographic features of the object. In one embodiment a three dimensional image is taken in a single flash to avoid blurring due to motion of the object. Thereafter a secondary pattern is projected to detect changes in the initial image. The images are processed in a computer program in a manner such that a complete 3D map of the surface of the object is obtained in digital form. Reiteration of the method can detect motional variation such as a breathing human, flexure of a complex mechanical structure, or a stress-strain testing of an airplane, vehicle, beam, bridge, or other structure.

28 Claims, 9 Drawing Sheets

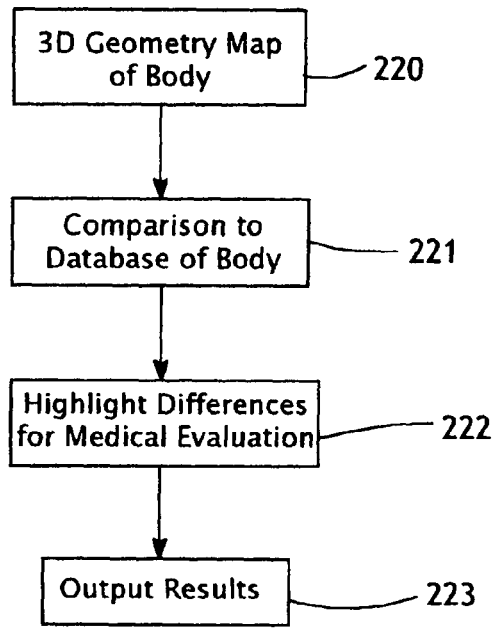
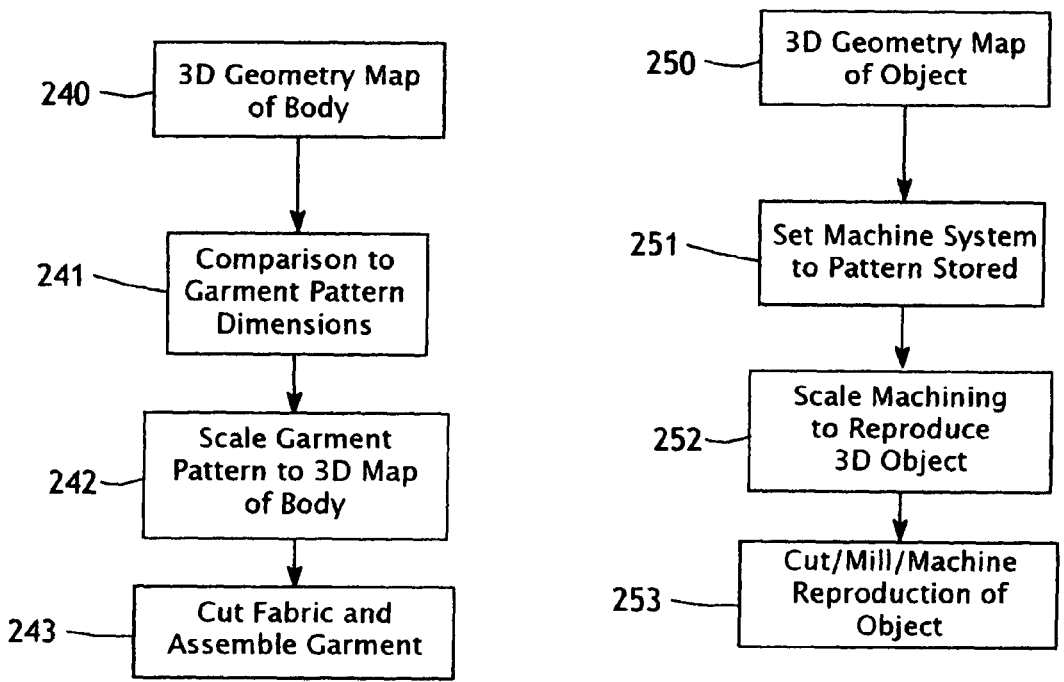
FIG. 12
FIG. 13
FIG. 14

METHOD AND APPARATUS FOR DYNAMIC SPACE-TIME IMAGING SYSTEM

CROSS-REFERENCE TO RELATED APPLICATIONS

This application is a continuation-in-part of application Ser. No. 10/966,095, filed Oct. 14, 2004, now U.S. Pat. No. 7,620,209 for which priority is claimed.

FEDERALLY SPONSORED RESEARCH

Not applicable.

SEQUENCE LISTING, ETC ON CD

Not applicable.

BACKGROUND OF THE INVENTION

1. Field of the Invention

The present invention relates to an apparatus and method for producing a rapid time-related three dimensional image with a numerical profile of an object. More particularly, it involves projecting complex digitally based patterns of electromagnetic waves (e.g. light) or scanning laser beams(s) on to the object, photographing these patterns with a fast response digital camera, and rapidly calculating a dimensional map of the contours, edges, and openings of the object. In a previous patent application Ser. No. 10/966,095, filed Oct. 14, 2004 we described the general technique for carrying out the method. In this patent we extend this general technique to describe several different systems. One system uses a high intensity single flash projector(s) to obtain un-blurred 3d images of a moving or still object. The second system uses a series of projections to provide more information, and also to provide time evolution information.

2. Description of Related Art

In 1905, Albert Einstein, who at that time was a patent examiner in Zurich, developed the Special Theory of Relativity which emphasized the importance of considering time in addition to the three dimensions of space in describing the behavior of matter and energy. In accordance with this concept, creating three dimensional profiling images in a very short time period is very useful in order to record a plethora of fundamental dynamic observations in physics, chemistry, biology, microscopy, medicine, and engineering. It also has a particular application to identification procedures for security applications.

Stereoscopic photography was invented in the nineteenth century, and has been developed since then to create very colorful stereoscopic movies. In contrast, the development of stereoscopic profiling with accurate detailed measurements of three dimensional objects has been difficult to achieve. The development of digital photography and fast computation using fast digital processing has now provided the possibility of accurate stereoscopic imaging with detailed dimensional measurements of the contours of an object in real time.

Presently used techniques for non-invasive three dimensional imaging with digital detailing of an object utilize a variety of systems. One technique is the use of time of flight of a pulsed laser where by the distance from the laser to the object is determined by measuring the transit time of the laser beam. This procedure, described by Cameron, et al in U.S. Pat. No. 5,006,721 provides fairly accurate digital topographical data. A commercial version of the laser ranging system is manufactured by Cyrax Technologies and several other companies. While such systems provide good three dimensional data, they involve a quite costly apparatus because the time of flight must be measured to a few picoseconds, and the mirrors used to direct the laser beam as well as the mirrors used to route the reflected beam must be exact to a small division of a minute of arc. In addition, the scanning of a three dimensional object with a laser beam requires a considerable length of time, due to the fact that each incremental point on the surface of an object must be illuminated by the beam and the time of flight measured, resulting in a finite (and relatively long) time for all points to be illuminated and surveyed.

Another technique for non-invasive three dimensional imaging is the use of stereographic projections of a grid. This procedure, as described by M. Proesmans, et al. In U.S. Pat. No. 6,910,244, issued Jan. 21, 2003, describes the use of a projected grid for topographic imaging. They describe a grid projection with a camera directed to provide three dimensional imaging. The use of such relatively static methods does not provide for the real-time measurement of dynamic details needed for dynamically imaging and measuring surface contour dimensions of objects which have movement, such as a bridge or beam undergoing stresses and strains. As stated in their patent, their application is "aimed at showing and not measuring the object."

Applications such as rapid engineering and reverse engineering with dynamic considerations of stress-strain relationships, measurements of flexure of mechanical and civil structures such as airplanes, vehicles, bridges, pipes, pipelines, steel tanks, autos and ships require very fast imaging techniques for which this invention is designed and applicable. In other applications as human body imaging where, due to walking, running, throwing, swinging, breathing and heart motion, it is important to consider the time aspect of imaging in order to acquire realistic measurements of the body. There is a need for such rapid imaging procedures in medical and sports an analyses, for example, in following the progress, and in determination of the efficacy of treatments of such diseases as osteoporosis and skin cancers as well as other skin and body medical and biomedical problems. There are many other industrial applications of this invention. The position and location of parts (of automobiles for example) on an assembly line can be measured quickly and accurately. The invention can also be used for wheel alignment. A major advantage of this procedure is that it provides better angular accuracy because hundreds of thousands of measurements are made instead of the relatively few measurements made with the earlier laser techniques. The fast acquisition time means images of moving wheels can be taken without blurring which leads to better accuracy because of better feature recognition. There are also many military and security applications from crime and forensic scene documentation to involuntary facial scanning to solving a jig saw puzzle: recognizing enemy assets from partial scans taken through trees and other opaque obstacles.

BRIEF SUMMARY OF THE INVENTION

The present invention utilizes a method for dimensional measurement of the surface contours of an object. The method employs selective computer controlled projection of a variety of patterns onto the object, and imaging of the patterns as they fall on the object to encode the topographic features of the object by analyzing how the images of the patterns projected onto the surface contours of the object cause the imaged pattern to diverge from the projected pattern. The object can have a motional variation such as a breathing human, a complex flexing civil or mechanical structure, or a stress-strain testing of an airplane, vehicle, beam, bridge, or other structure. In the present description even faster motions can be accommodated with no blurring. Such motions could be associated with spinning wheels or walking patients. The images of the object are collected by a digital camera, and are processed in a computer program in a manner such that a complete three dimensional map of the surface of the object is obtained in digital form. In order to facilitate precision, the system may generate a digital pattern which is projected onto the object in a manner so that the pattern configuration provides the data for a computer program to determine exact dimensions. The system may also use a laser source of radiation by scanning the object rapidly using a laser beam. By utilizing a rapid procedure and reiterating it, the data provides a measure of the time variations of the size of the object. The usual output of the digital system supplies a three dimensional true color image as well as exact dimensional data on the depth, width, height and contours of the surface of the object. In one configuration, a pattern of colored lines is projected onto the object and all of the data for the 3 D view is obtained in a single camera shot. Advantages of the single shot are:

1) fast enough to eliminate mechanical motion effects of the object;
2) minimizes heat;
3) can obtain 3-d images in outdoor lighting;
4) projector and camera combination are light enough to be portable.

In another configuration the projector illuminates continuously, and the motion of the object can be studied by measuring differences from an initial 3d image.

The invention is particularly applicable to imaging of humans for medical analyzes. Some examples: for full body inspection for skin cancer wherein the size of skin malignancies can be monitored, for breathing patterns, for reconstructive surgery, for dental analyses of the jaw, individual teeth, and bite, for facial reconstruction, and for gait analysis. It is applicable to design and manufacture of prosthetic units. Likewise, the invention may be used to monitor the changes in the body overtime to assess the efficacy of weight loss programs, body building efforts, and the like. The system is also applicable for body measurements for the fitting of custom clothing and custom shoes, wherein all dimensions of the body are acquired, and clothing patterns may be modified in every dimension for optimal fit.

The present invention is designed to determine exact measurements as distinguished from relative topographies. In order to carry out such exact measurements, a range finder system and/or a standard fiducial object can be utilized in the system so that absolute dimensions are determined.

The invention is also useful for identification and recognition for security applications, as it can provide motion detection and trigger three dimensional mapping of an intruded area. Also it is very applicable to accident analyses and prediction of mechanical failure where dimensional changes in mechanical structures may be analyzed in three dimensions. The invention is also very useful in imaging the holds of ships, planes, freight trains, and warehouses, where the images may yield numerical values for the exact amount and distribution of space available for use, or when partially loaded, for a determination of the space available for further use. Another application is for security in examining the cargo space in ships, trucks, planes, and other compartments; i.e., by determining the volume numerically exactly so that the existence of hidden compartments can be found. Another application is to microscopy. Here the three dimensional sizes of the object, (for example, a microbe), are readily determined, and the mobility of the microbe may be measured. Recent research also indicates that weaponized microbes in a cloud can be identified by the reflected light spectrum and by the change in shape of a cloud. This invention provides a significant advantage over the usual two dimensional measurements used for microscopic analyzes.

In a further aspect of the invention, by utilizing a plurality of distinct wavelengths within the electromagnetic spectrum, with the appropriate projectors and digital cameras, infrared, ultraviolet, or any special type radiation may be utilized to acquire and reconstruct three dimensional images. The use of infrared is particularly appropriate for obtaining three dimensional thermal images which provide important information about temperature variations in humans, animals, electronic equipment, and mechanical structures. For such applications, the projector(s) are equipped with emitters and the digital camera(s) are equipped with sensors that are sensitive to infrared. Likewise ultraviolet radiation may be used. Another application is in inspection of manufactured products. Misalignments, displacements, or other defects are readily detected by comparison of the three dimensionally mapped color image with a stored image of the correctly configured product. One such immediate use is applicable to quality control of manufactured items, such as integrated circuit inspection. Another immediate use is in the production of wallboard (or sheetrock), in which each sheet must be examined for superficial imperfections as well as surface non-planarity. Currently wallboard sheets are examined inch by inch by a scanner system, but a single imaging sequence of this invention at high speed may check an entire sheet at once. This invention could also be used to measure the dimensions and locations of parts such as doors, fenders, etc. on automobiles as they move through the assembly line.

BRIEF DESCRIPTION OF THE DRAWING

FIG. 12 is a functional block diagram depicting the method of the present invention applied to generating a dimensional map of the human body for medical purposes.

FIG. 13 is a functional block diagram depicting the method of the present invention applied to generating a dimensional map of the human body and fashioning custom clothing from the map.

FIG. 14 is a functional block diagram depicting the method of the present invention applied to generating a dimensional map of an object and using automated machining to create from the map a copy of the object.

DETAILED DESCRIPTION OF THE INVENTION

Figure 1:
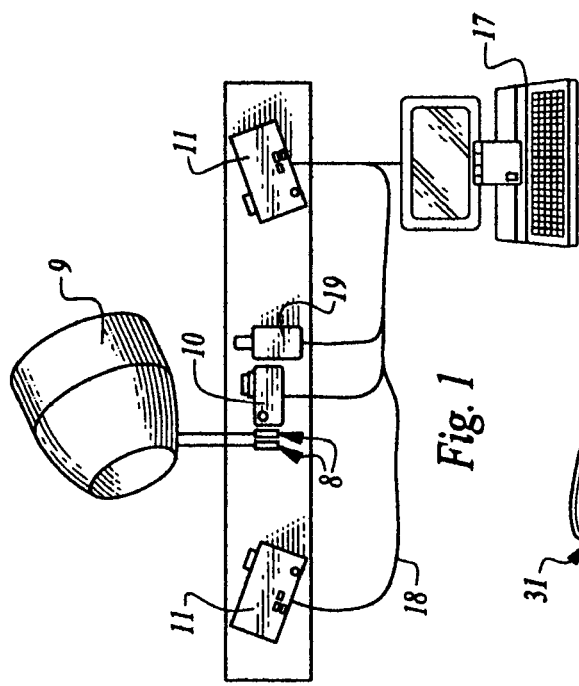
FIG. 1 is a schematic overhead view of a layout of a single camera, two projector imaging system designed for rapid three dimensional dynamic imaging in accordance with the present invention. For many applications a one projector-camera combination is sufficient.

The present invention generally comprises a method for generating a three dimensional map of the surface of an object, and analyzing the dimensional data to examine the object in useful ways. Referring to FIG. 1, the method involves providing a pair of projectors 11, each of the projectors directed to project a pattern of colored lines on an object 9. A single flash projector may be composed of a flash lamp and a patterned source or a digital projector. The flash lamp provides high intensity light for a short time. This has two advantages: it allows the fast study of mechanical position without image blurring and it avoids heating the object while still providing enough light to illuminate the object. The projectors are separated and spaced to illuminate differing aspects of the object. A digital camera 10 is directed at the object 9 to acquire images of the object, and the configuration of the projected patterns of colored (or black and white) lines on the surface of the object. The images are fed to a computer 17 which processes the images to generate a dimensional map that numerically describes the contours, edges, openings, and surface features of the object 9. Note that for the single flash projector, the one-projector camera system is light enough that it can be held in the operator's hands while taking shots from different angles or views. Motion induced by the operator's hands is not important because the single shot data acquisition is so fast. In some cases it may be desired to obtain the full 3 dimensional image of the object from different perspectives. Multiple projectors and/or cameras can be used to obtain views that would be occluded if just one projector camera pair were used.

By using multiple projectors 11 and the camera 10, the images generated by the camera can readily be processed in a manner wherein they mesh together seamlessly, and a full three dimensional digital image of the object 9 is obtained. The apparatus may be rotated about the object, or the object may be rotated while the apparatus is stationary, so that all the surfaces of the object 9 may be imaged and dimensionally mapped, if desired or necessary. The projectors and camera are all under the control of the computer 17 which sends out control signals and also receives the imaging data which it processes to obtain a complete three dimensional image. The seamless joining of the different views is accomplished in software by observing that when several adjoining profiles from the different views are found to be identical, then that is the seam between those views, and the different views are then joined in the display and in the numerical values of the stored profile information.

The exact fiducial measurements of an object are obtained by initially scanning an object with well known dimensions. The system uses that scan as a calibration for further scans. The object is scanned from many different angles or views. The calibration of the fiducial measurement has the advantage that this known calibration is the same for all views.

The computer program used to process the images of the patterns projected on the object 9 obtained by the digital camera 10 utilizes the shapes of the projected lines to determine the curvatures, edges, openings, and hills and valleys of the object. The computer 17 is programmed to carry out the mathematical function that determines the numerical profiles of the object. In order to obtain a sharp focus of the projector images, the camera, which is easily automatically focused, may also provide a focusing signal for the projector focusing system thereby providing sharp patterns to facilitate the three dimensional map determination.

The projectors 11 and the camera 10 are specified to operate using any of several types of radiation. White light is used when true color image construction is desired. However, in some instances, infrared, ultraviolet, laser, or X-ray radiation are of more importance or of more interest in imaging. The cameras and projectors may be utilized for such procedures by simply substituting infrared, ultraviolet, or X-ray sensitive cameras, projectors as appropriate to the wavelength utilized.

The projectors 11 are programmed by the computer 17 through the cable 18 to provide a series of patterns having lines extending vertically and/or horizontally which are bent or deformed when they are projected onto the surface of the object. The digital camera 10 receives the image of these deformations in the numerically ordered pixels of its photosensor, the pixel data being in the form of numbers which determine the entire topography of the object. These ordered numbers are then transmitted via the cable 18 to the computer 17 which processes and assembles these numbers to provide the complete dimensionally mapped topographic image of the object. The computation may be accelerated, if necessary, by using multiple processors coupled together. The cost of such high speed computation has become quite reasonable due to progress in computer manufacturing.

A variation of the single shot system can be employed to obtain dynamic or motional information, A single pattern is projected continuously (or with rapid repetition) on the object 9. The pattern image caused by the topography of the object being scanned, which may vary in time, is then digitally acquired at a fast frame rate which, depending upon the type of digital camera, may be 30 times per second, hundreds of times per second, thousands of times per second, or more.

The variations of the dimensions of the object, as revealed by successive dimensional maps taken over time, provide a time sequence of the dynamic changes of the object.

In reconstructing the image from the calculated dimensional map, a spline fit is utilized to smooth the digital data. This results in a type of "best average" for the image display, and the image is presented smoothly rather than as discrete steps common to some digital displays.

Figure 2:
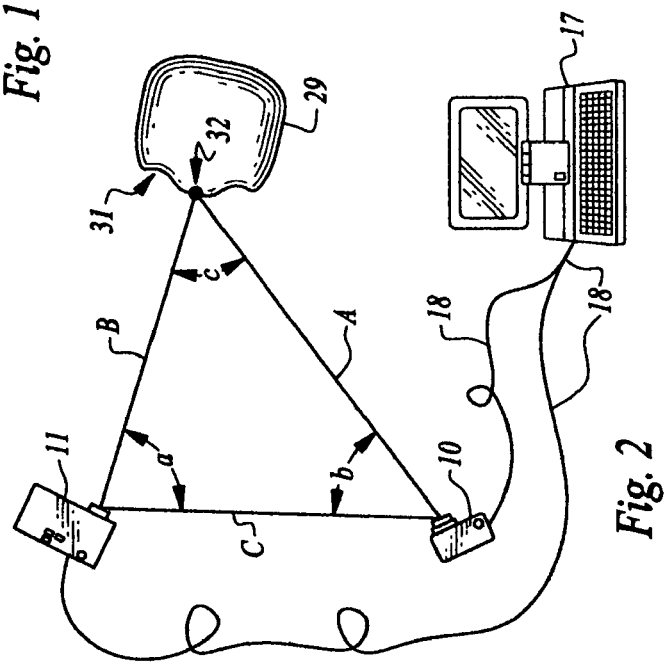
FIG. 2 is a schematic view of the geometry of the imaging system of the invention showing the triangulation procedure utilized to obtain an image of the exact profiles of a three dimensional object.

Referring to FIG. 2, the fundamental measurement of the exact distance from the camera receptor plane to the object utilizes a trigonometric solution of the oblique triangle, one side of which B is formed by the light ray B projected by the projector 11 to the point 32 on the surface 31 of the object 9. The digital camera 10 receives reflected light from that point 32 along the direction A which forms a second side of the triangle. The distance C which forms the third side of the triangle is the exact distance between the projector and the camera. The angles a and b of the triangle are known quantities because they are established by the geometry of the setup and the digital information supplied to the projector and received by the camera. Therefore, using trigonometry, the digital computer 17 calculates the exact distance A from the camera receptor 10 to the object surface 32 using the following formula:

$$A = C \sin a / (\sin c) \quad (1)$$

Since C, the distance between projector and the digital camera is known, and angles a and c, the angles of the directions of the projector and the digital camera are known, the calculation is rapid and straightforward. The computer calculation is facilitated by having the sine values in memory so that the sines of the angles are rapidly accessed. In this invention, the values of all the distances to the object are simultaneously calculated for all of the pixels of the camera, each of which are, in general, different values. This separation of all of the distances to the different picture elements (pixels) of the digital camera occurs through the fact that each pixel (the smallest useful image increment) provides its individual value for the distance to the object because of the geometry of the photosensitive receptors of the digital camera. In other words, the individual pixels are processed by the formula (1), and provide a complete set of distance values simultaneously.

In order to carry out all the calculations for all of the points on the surface rapidly, it is necessary to carry out many calculations almost simultaneously. This is accomplished by projecting a pattern of many lines on to the surface of the object, and using the digital camera which, due to its numerical pixel construction, automatically labels each individual point. All of these points are then transmitted to the very fast computer 17 which assembles the point calculations of distance, (from the camera to the surface of the object), into the complete image. This procedure provides a complete profiling of the three dimensions of the surface of the object (a three dimensional map), including all the hills and valleys, edges and openings of the surface of the object 9 (or 29).

In general, object surfaces are time dependent, as for example, a stress-strain relationship or some other time dependent induced variation or motion. To measure these time dependent effects, first the complete image is calculated, and in the final step of that procedure, the projector projects many fine lines at one time on the object surface. All of the distances to every point on those lines are accumulated in the computer memory. When the object surface flexes or moves in any mode, the line pattern changes its curves and distorts proportionally to the nature of the surface change. The digital camera records all of the variations and transmits it to the computer 17. The computer compares the new data with the stored data. This comparison is a very fast procedure for a computer. Using this procedure, the measurement of time dependent changes of the object surface 31 is very fast; the limitation on the speed of imaging time-dependent changes in the object is the speed of available digital cameras which, at the present time, can be considerably faster than one hundredth of a second, and even one thousandth of a second. A continuous (or rapidly repeating) projector that is needed for motional and time evolution studies may be a modification of the single shot projector. For the first set of 3D views the normal single shot pattern is used and the regular 3D image processing is done. A second pattern consisting of closely spaced lines is projected that has a fast repetition rate which is synchronized to the camera with its high repetition rate. The data for the standard flash with colored lines is acquired fast enough to avoid blurring but it takes several seconds to process even with fast multiple computers and this is not fast enough for real time studies. This image from the second pattern is sufficiently accurate and fast enough for real time studies but it requires the 3D reference from the first pattern. For the study, the reference is established in several seconds or less and then data is updated every ~10 msec or even faster.

The projector with its projected pattern can be replaced with a programmable digital projector with a high repetition rate. This two-pattern technique has very fast processing so that it can provide a real time display of the 3D motion. By taking fast repeating images with color striped patterns one can accommodate a large range of motion.

In order to have a reference image, a mathematical procedure is utilized which places an imaginary plane in the scene, solves for its expected values, and uses it as the reference. This solution both greatly decreases noise and halves the number of images, and thus time required. Mathematical logic is included to remove the effect of perspective inherent in cameras. The camera "sees" close objects as larger and farther objects as smaller. Since the 3D imaging system has recorded the distances to objects it can correct for this inaccuracy. Because modern photo receptors have greater resolution than current LCD projectors and other types of projectors, the system uses the camera's increased level of detail to augment the level of accuracy provided by the LCD or other types of projectors alone. Logic is included which regards each resolved line from the projector as a discrete block of many pixels and, after analysis, smoothes these pixels intelligently using conventional spline fitting procedures.

Figure 3:
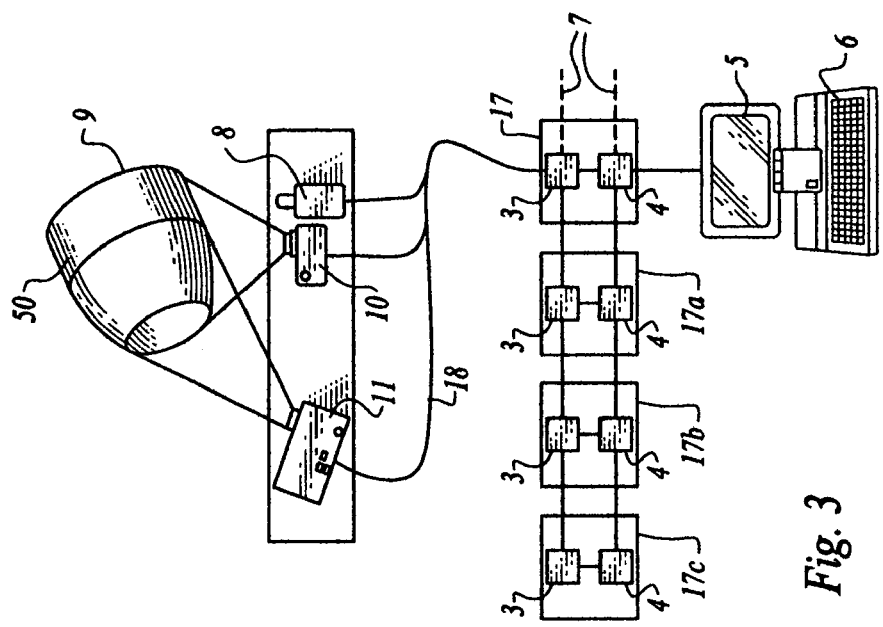
FIG. 3 is a schematic view depicting a multi-processor layout for high speed image acquisition and conversion to three dimensional data.

Referring to FIG. 3, the lines 50 projected onto the object 9 by the projector 11 are very closely spaced and provide the basis for a very fast imaging procedure. These are projected as a set of very fine lines, and are perceived by the digital camera system as a large collection of points because of the fundamental nature of the image receptor which is divided into picture elements, (pixels). With a digital camera system having 10 million pixels, for example, the camera receives 10 million points of excitation each of which has an exact geometric relationship through Formula (1) to the angle of the lines from the projector. Each of these 10 million pixels transmits its value directly to the computer memory 17 which interprets each value according to formula (1) as the actual distance from the camera photo receptor to the surface of the object 9. The computer calculation is almost instantaneous due to the fact that the computer memory holds all of the sine values for immediate access. The procedure is sufficiently fast that it may be considered as happening in real time. The transformation of the calculated distances into the actual numerical profile values of the three dimensional map is also very fast because that only requires a scaling factor. The scaling factor is a simple multiplication factor for the computer and that calculation takes place in less than a millisecond.

The scaling factor is obtained by an initial observation of a specific projected line which is detected by the digital camera and then calculated through formula (1). Alternatively, the scaling factor can be obtained by imaging an object which has an exactly known size (a fiducial object), or by using a projected scale.

Once the entire calculation of the profile (a dimensional map of the surface) of the object is obtained, the time variations of the size of the object can be very readily calculated because the time changes in the pixels of the camera change the values transmitted to the computer memory, and these changes are immediately recorded by the process of subtracting the values of each set of data points from the values of the prior set of data points. In the computer, the subtraction operations are extremely rapid by the nature of computer design.

The computer utilized can be a very fast computer, but if extreme speed is required it is more economical to couple a number of computers 17, 17a, 17b, 17c, (and as many as one desires for the selected computer speed) together as shown schematically in FIG. 3. Each of the computers is coupled together via high speed network cabling, and a high speed network switch within the memory compartment 3, and the central processing modules 4. The coupling allows all of these computers to work in unison and provide very fast calculations. The terminal display 5 and the keyboard 6 provide a control and response display. The dotted line 7 indicates that the system is not limited to four computers, but may be extended to more computers if additional speed is desired.

The features regarding the speed of this system provides a basis for dynamic imaging, which allows for the following applications in addition to being able to very rapidly provide imaging of non-dynamic objects.

1. Dynamic observations and measurements of deformation of aircraft wings under stress-strain conditions.
2. Dynamic observations and measurements of deformations of bridges and other structures under stress-strain loading conditions.
3. Dynamic observations, measurements, and detection of moving objects for security purposes.
4. Dynamic observations and measurements of human bodies including the aspects of breathing and movement: e.g., gait, throwing, running, walking, swimming, swinging, and hitting (e.g. golf swing).
5. Dynamic observations and measurements of objects which fail under load, with determination of the failure mode.
6. Dynamic observations and measurements of humans for security analysis and identification based on three dimensional images.
7. Dynamic motion studies with numerical analyzes with application to human walking, human prosthetic design, human medical condition analysis.
8. High speed quality control processing in which a product such as wallboard or sheetrock is examined by the system of the invention, the entirety of each sheet being examined at once in a single imaging sequence and analyzed for surface defects or surface non-planarity.

Other applications of the invention to non-dynamic objects (not subject to significant movement) are:

1. Mapping of a wound in a human or animal body, so that an appropriate dressing may be constructed quickly and accurately.
2. Mapping of a damage site in a metal, concrete or other fixed structure, to determine their suitability to continue to perform, or determine expected time before failure.
3. Mapping of corrosion pits in a pipeline or other critical structure, whereby rate of corrosion (rate of deterioration) may be observed and monitored and treated.
4. Inspection of goods during and after manufacture for quality control, process control.
5. Mapping of objects for use in CAD/CAM production of copies; scaling of mapped objects to scale up from model size to full size, or vice versa.
6. Inspection of railroad rails to detect and determine maintenance and repair situations.
7. Measurement of dimensions of human body or animal body to determine effects of diet or of medical treatments.
8. Measure the dimensions of injured portions of bodies to aid in constructing prosthetic parts or devices.
9. Mapping of dentition and oral cavity to aid in fabricating dental devices or prosthetics.
10. Mapping building structures, rooms, and/or configurations to aid in architectural design or contracting building and modifications.

Figure 4:
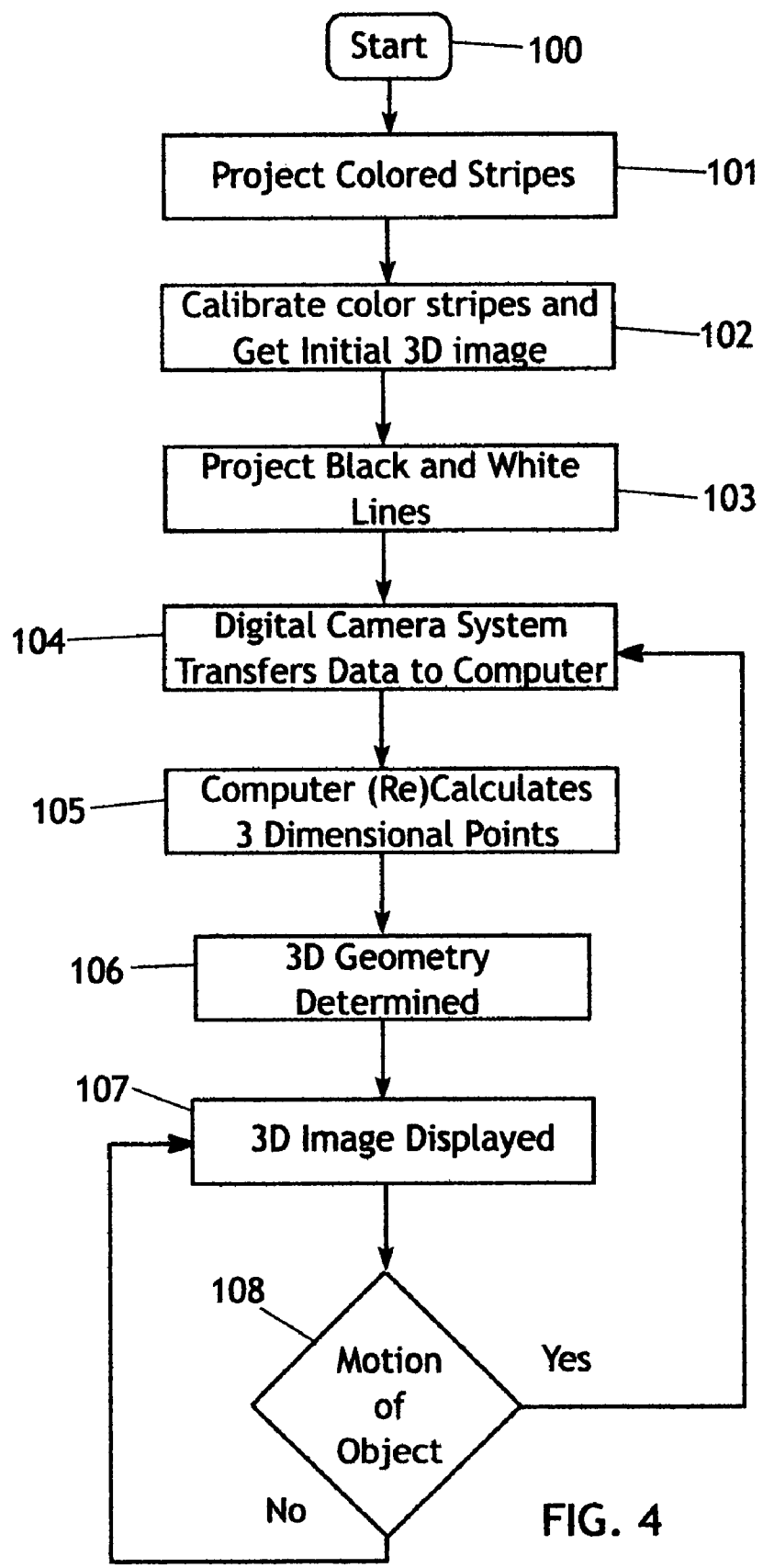
FIG. 4 is a flow chart depicting a procedure for speeding up the dynamic imaging procedure.

Referring to FIG. 4, a flow chart of the computation as controlled and calculated by the computer is shown. This process is for the real time acquisition and display of 3D motion. This motion has to be within the field of view of the scanner. After the start 100, in the first step 101 the projector, controlled by the computer, projects a single flash pattern of colored stripes onto the object which is to be scanned. The digital camera system, which is synchronized through computer control, takes the initial image which is processed to provide an un-blurred 3D image of the object in step 102. This processing provides not only the initial 3D image but also tells what plane is associated with each vertical colored stripe. After this initial processing which can take several seconds or less the standard color source is replaced with a black and white source that has a large number of closely spaced vertical lines. Each line in this pattern is assigned a plane based on the calibration from the image data derived from the color stripes. In step 103 the projector projects this pattern of fine lines which the digital camera system images and transfers in step 104 to the computer. The computer then calculates in step 105 all of the distances from the camera to the surface of the object. This calculation is very fast (~<10 msec) because it does not have to recalibrate the plane locations for each stripe. Using these data, the complete three dimensional geometry of the surface of the object is obtained in step 106, and a three dimensional rendering of the object is constructed and displayed in step 107 on the computer screen.

It is generally likely that the object will have some movement. Consider a breathing human, or an aircraft wing under a variable stress as simple examples. The motion causes a change in some of the pixels of the digital camera. A digital camera can, for example, take 1,000 images per second. Since the movement of the object is typically very slight in one thousandth of a second, only a few pixels in the camera will be changed in that short a time span. In step 108 the current image is subtracted from the previous image to determine which pixels have changed. There are typically only a few points that need re-calculation in the short time span. Therefore the computer can easily do the re-calculation in much less than a thousandth of a second. The new three dimensional geometry in reiterated step 106 is determined very rapidly, very nearly as fast as the object can move, since there are typically only a few point to recalculate to update the existing 3D geometry data. Consequently, this system provides complete motion information about the object. In other words, three dimensional imaging is obtained in real time for moving objects.

Because a digital camera can provide data at rates in the range of one frame per thousandth of a second, and the computer can easily do re-calculations for the incoming data at a rate of much less than a microsecond, and an object generally moves very slightly in such a short time span, three dimensional movies constructed of the machine-rendered images are practicable.

For a small change, there is no need to recalculate and re-render (105) the total image. Such changes are perturbations on the whole image as defined in mathematical analyzes. Therefore these small changes in the image can be referred by the camera back to the existing pattern in the computer, and the computation 105 is limited to the changes only. That procedure greatly shortens the time needed for the display of the new image relative to recalculating all of the image data. By this method, the variations in such objects, for example, as aircraft wings under test, testing of humans breathing patterns, and bridges under load can be analyzed in real time with all of the measurements recorded in the computer memory.

Referring to FIG. 3 again, when time permits, the system consisting of one projector 11 and one camera 10, with or without one range finder 8 may be utilized. In this case, when it is desired to record and reconstruct the full 360° image of the object, the camera, projector and range finder may either be rotated about the object, or the object may be rotated to obtain the full 360 degree view. In some cases, one may use a single camera 10 and projector 11 and one view since one then will obtain a three dimensional image of the region of the object that is scanned.

Figure 5:
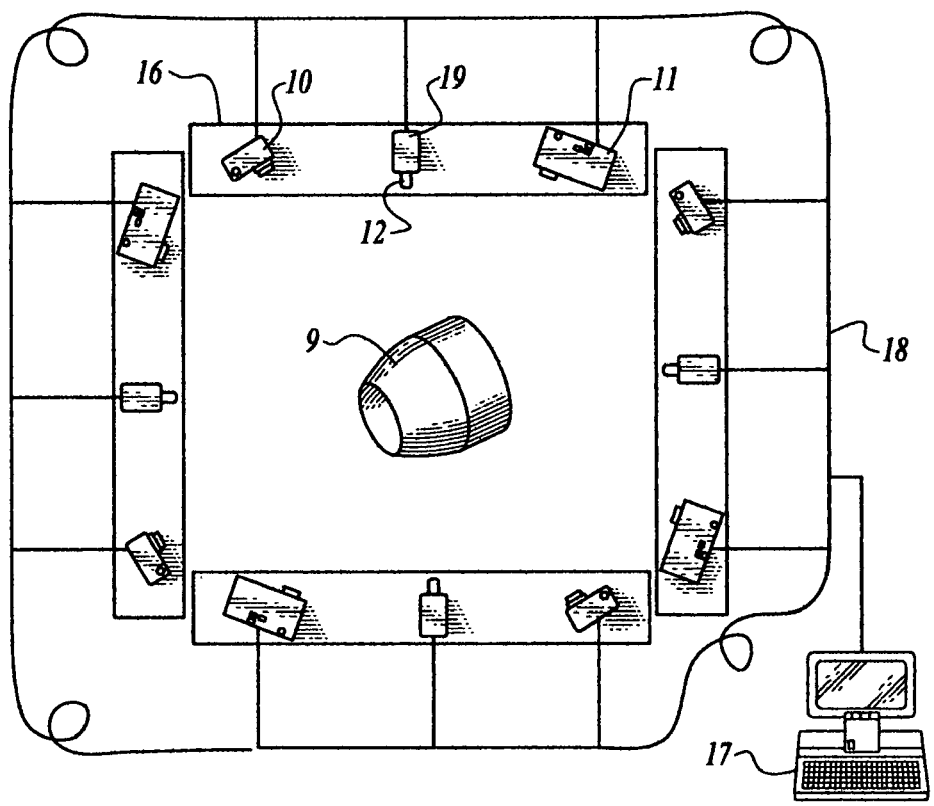
FIG. 5 is a schematic overhead view of the layout of a four projector, four camera system which can be used to obtain three dimensional dynamic images.

Referring to FIG. 5, by using four cameras 10 and four projectors 11 arrayed in gene rally Cartesian directions, the system can very rapidly capture the front, sides, and back views of the object 9, each of the projectors providing a computer generated pattern of lines on the object. However, in some cases, it may be adequate and economically advantageous to have three projectors and cameras. The different views are all seamlessly assembled by the computer program since each overlap of a pattern is numerically redundant and provides the same data information. Each camera can take data from any of the projected lines within its field of view.

Figure 6A:
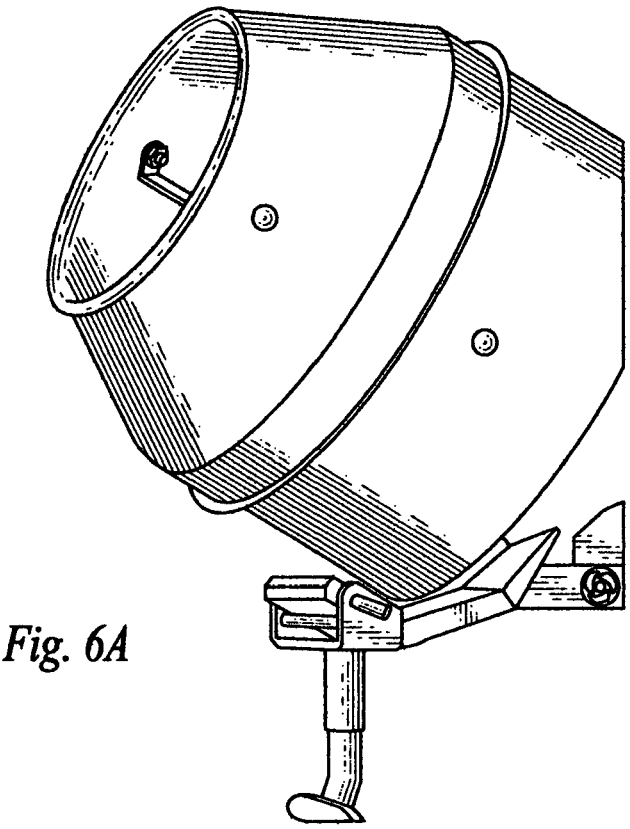
FIG. 6A-6B are images of a cement mixer, which can be operated during the imaging procedure, using the invention to image and develop a dimensional map of the exterior surface of the mixer, and show various dynamical stresses based on dimensional variations observed in real-time.
Figure 6B:
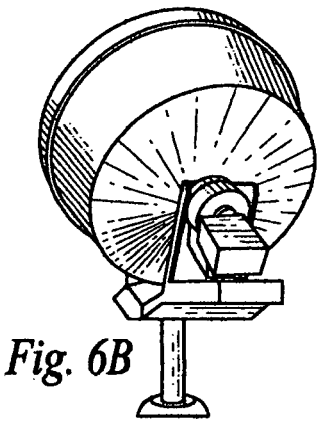

FIG. 6A portrays the image of a cement mixer shown in a side view. This image is reconstructed using all of the data assembled by digital camera(s) and projector(s), as arrayed in FIG. 1, 3, or 5. All of the dimensions of the cement mixer are stored, and are then utilized to rotate and re-size the cement mixer as shown in FIG. 6B.

Figure 7A:
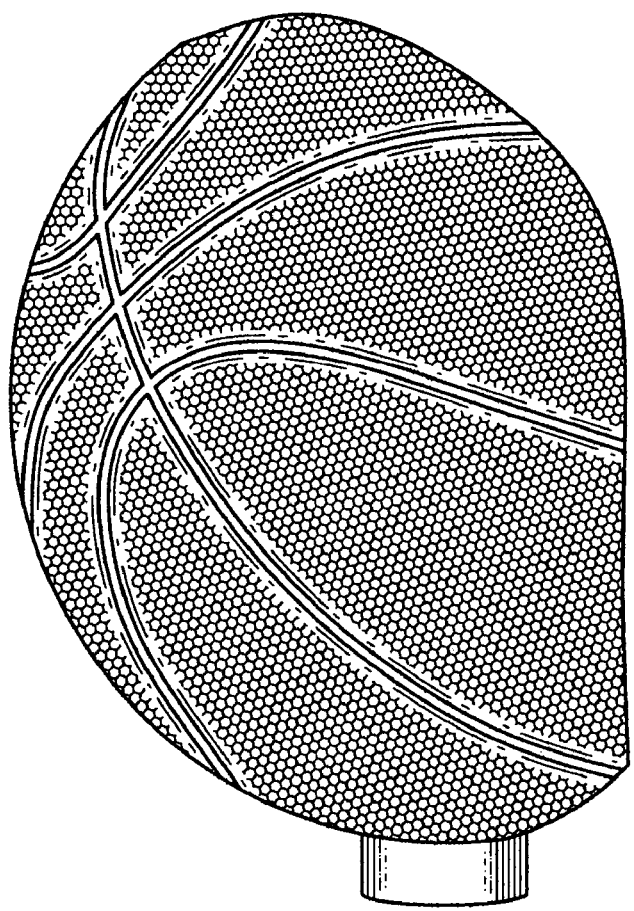
FIG. 7A is an image from a scan of a basketball.
Figure 7B:
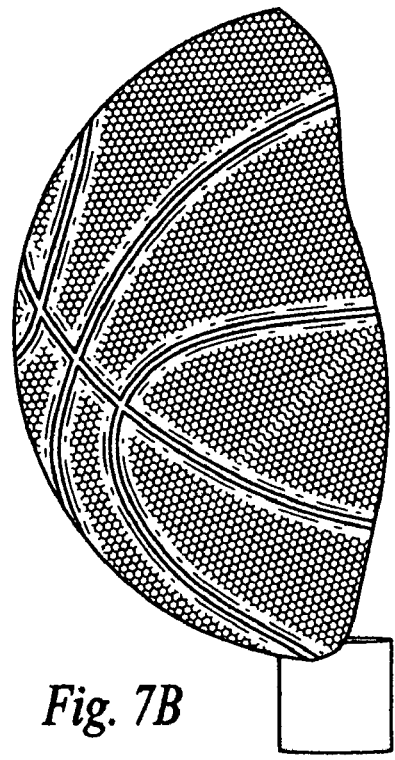
FIG. 7B is an image of the basketball computer-generated and rotated using the stored numerical dimensional data obtained from the scan procedure.

FIG. 7A depicts a three dimensional image of a portion of a basketball in a front view. All of the dimensional information of the basketball is stored in the computer, and is then utilized to rotate and compress the image as shown in FIG. 7B. Although there are no distinct surface features to note on the basketball, the fact that the rendering in any rotation is smooth and spherical is an indication of the accuracy of the method of the invention.

Figure 8B:
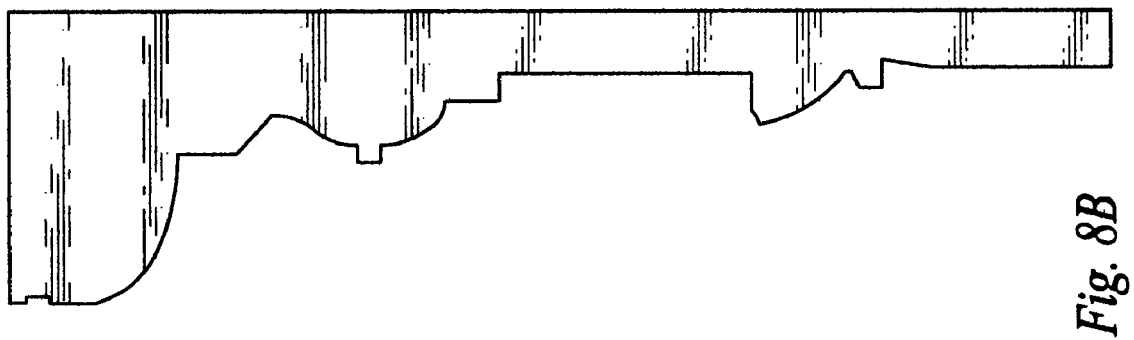
FIG. 8B is an enlarged image of the profile of the molding of the piano computer-generated from the numerical data obtained in the scan process.
Figure 8A:
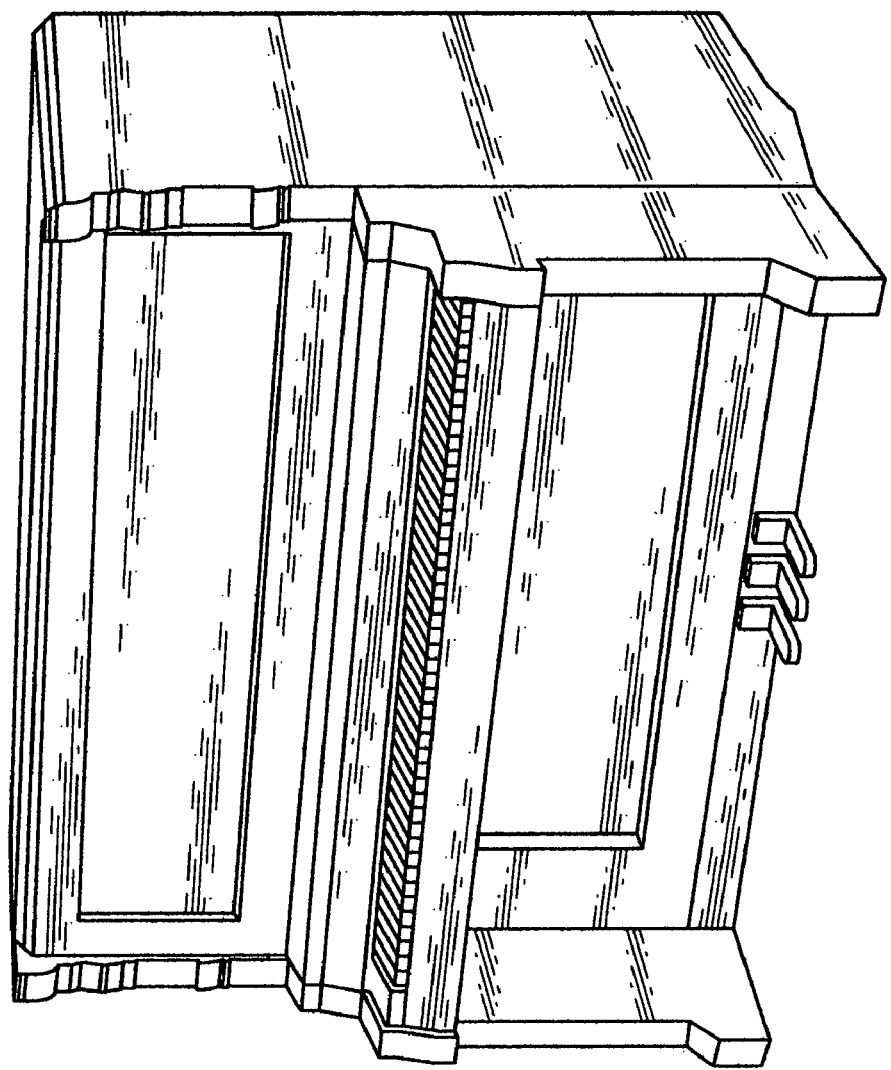
FIG. 8A is an image from a scan of an upright piano.

FIG. 8A shows a rendered image of an upright piano based on all of the digital information about the profile of the piano determined by the method described above and stored in the computer. FIG. 8B is a magnified profile of a portion of the piano, showing in profile the relief detail of the piano molding. It is apparent that the method of the invention is capable of resolving minute surface variations over the entire object, and rendering them clearly.

Figure 9A:
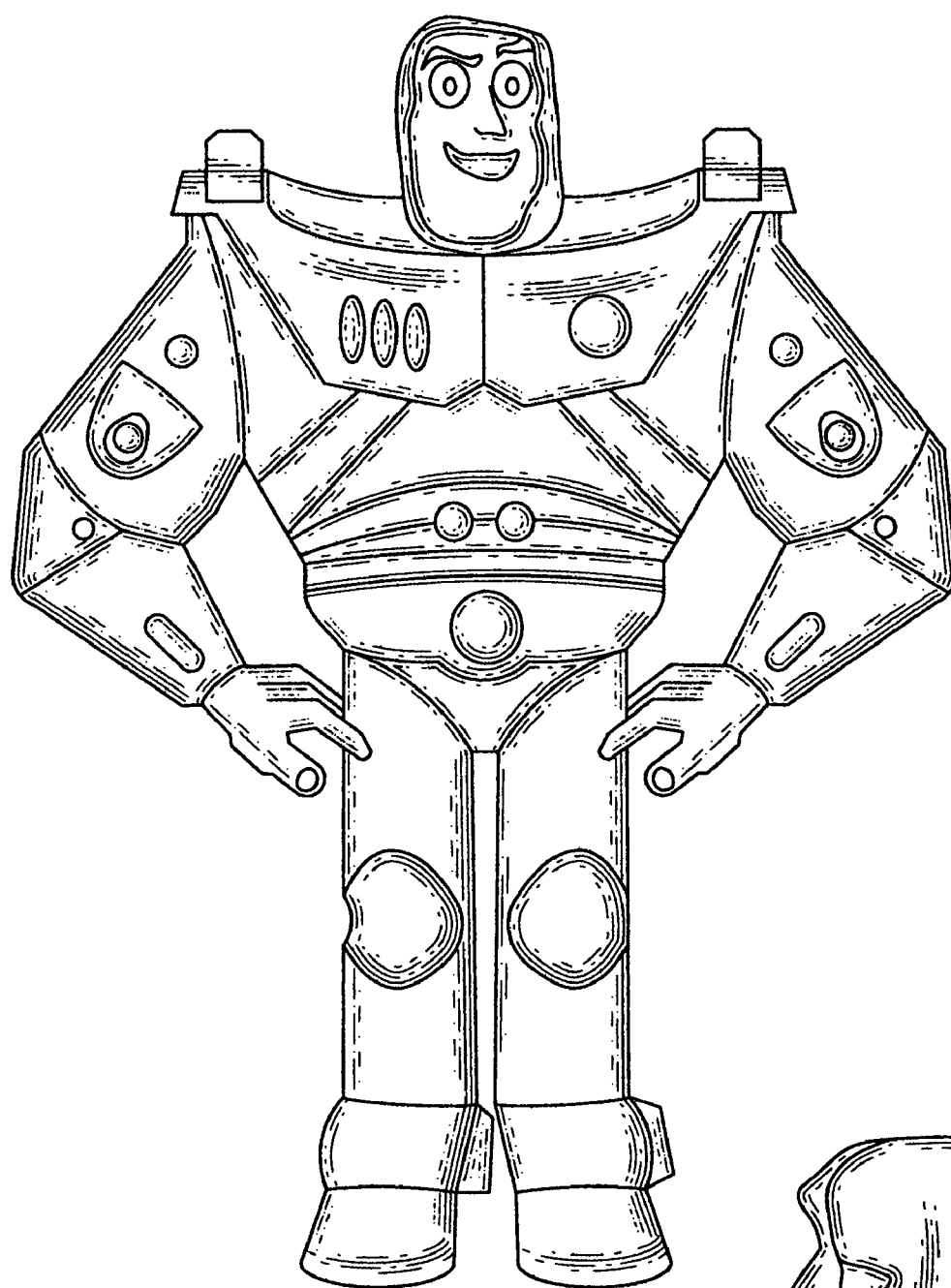
FIG. 9A is an image of an automated movie doll. The image shows the detailed set of points accumulated in the scan on the left.
Figure 9B:
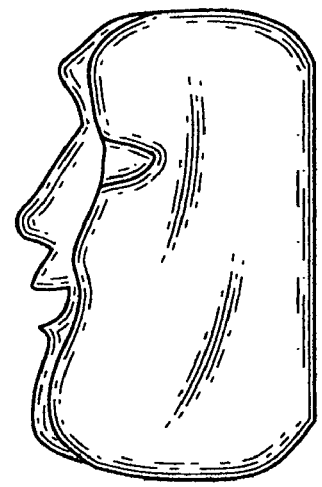
FIG. 9B is a computer rendering of the complete dimensional map image.

FIG. 9A depicts the rendered image of a toy based on all of the digital information about the profile of the toy determined by the method described above and stored in the computer. The reconstructed facial profile of the toy shown in FIG. 9B depicts the power of rendering from the dimensional database obtained by the invention.

Figure 10:
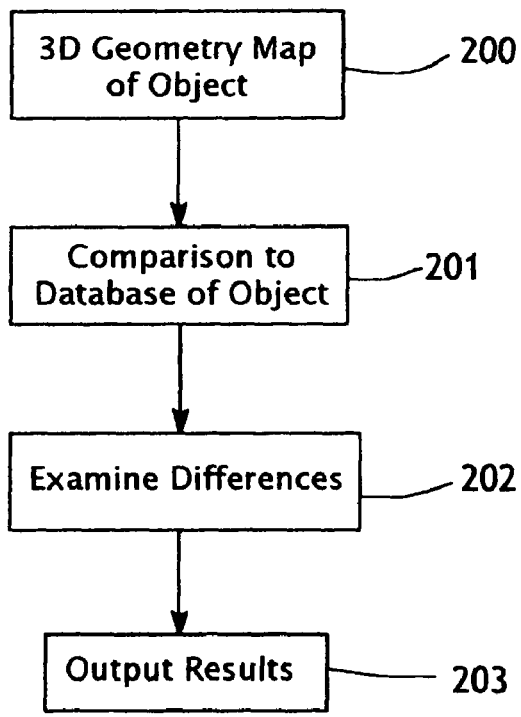
FIG. 10 is a functional block diagram depicting the general method of the present invention for generating a dimensional nap of the outer surface of an object and applying the useful results therefrom.

FIG. 10 depicts a flow chart showing the general method for applying the three dimensional display and measurements of a solid object to achieve useful results In step 200 the process of imaging and calculating the 3 D geometry of the object. The map is compared to an existing database of the object in step 201. In step 202 the differences between the map and database are adjusted for a best fit and examined, and the final step 203 the differences are reported in a useful format. The object database used in step 201 may be obtained from prior records of design, CAD files, and the like, or from previous dimensional maps obtained by the invention in prior time intervals ranging from portions of a second to months. The output of step 203 may comprise a graphic map depicting changes overlaying an image of the object and portrayed in false color, or contour lines overlaying the image, or other graphic-techniques that highlight areas of dimensional change and interest.

Figure 11:
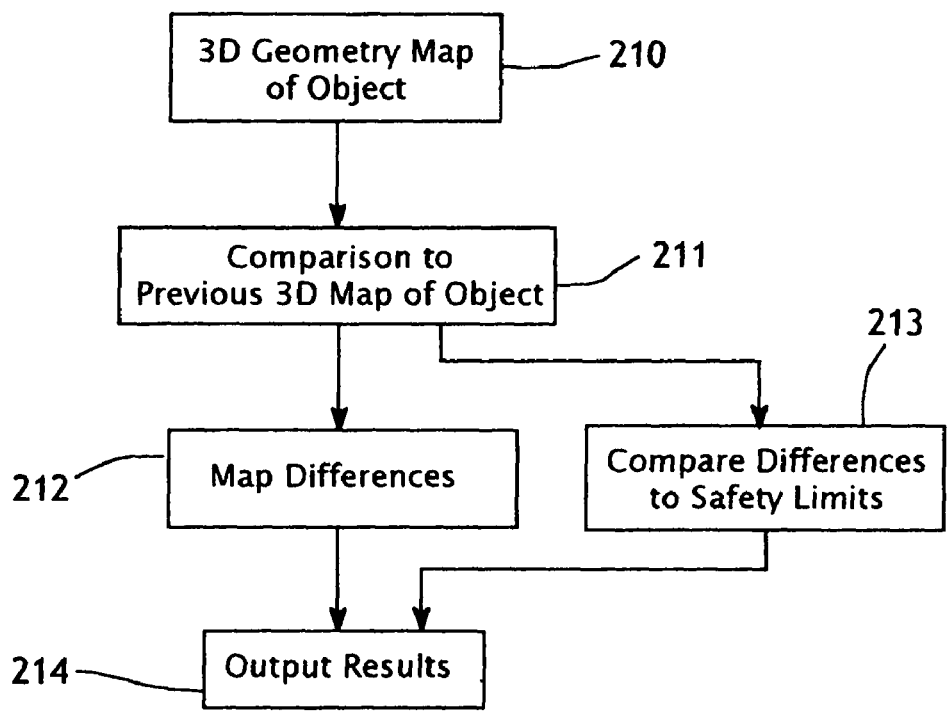
FIG. 11 is a functional block diagram depicting the method of the present invention applied to generating a dimensional map of the outer surface of a moving object.

FIG. 11 depicts a flow chart representing the dynamic imaging of an object or person in motion or exhibiting movement of at least some portion, starting at step 210 with obtaining the most recent 3D geometry map from the most recent image scan. The scan is then compared to the previous 3D map in step 211. The differences are then compared in step 212 and mapped into the output 214. In step 213 the differences are compared to a safety limit (dimensional tolerances) to determine if the object is approaching or exceeding a tolerance limit. For example, a tank undergoing pressurization may expand normally, but it may also distort in some areas, indicating a potential failure mode. In the example above of quality control processing for wallboard and sheetrock, the 3D map of the surface of each sheet may be compared to an ideal planar surface to highlight any surface defects or surface curvature. If the differences for any sheet exceed quality standards, the sheet will be rejected.

Referring to FIG. 12, a method for treating the human body begins at step 220 with imaging and calculating the 3D geometry map of the body as described above. The 3 D geometry map of the body 220 is compared in step 221 to a database containing the stored 3D geometry map(s) of the body 221. The differences are then computed and highlighted in step 222 for medical or health evaluation, and the new image is outputted in step 223 with the differences highlighted. This method may be used to assess changes in the body over time for medical purposes, and also may be used to evaluate weight loss programs, body building regimens, and the like.

Referring to FIG. 13, a method for determining sizing or custom manufacturing for a suit, dress, shoes, or other garments, begins at step 240 with imaging and calculating the 3D geometry map of the body (or relevant portion of the body). The 3D geometry map is then numerically compared in step 241 to the garment pattern dimensions. The garment pattern is then scaled in step 242 so that every seam will extend in a best fit to the mapped body. In step 243 the garment fabric is then cut according to the scaled pattern and assembled. This process produces an optimal fit to the individual body, despite the wide range in human body types and sizes. In a similar vein, the 3D geometry map of the body may be used instead to select the best fitting pre-manufactured garments, based on a complete comparison of data on existing garments with the 3D geometry body map of the invention.

Referring to FIG. 14, a method for reverse engineering or reproduction of an object begins at step 250 with the initial scan that provides a 3D map of the geometry of the object. The 3D geometry data is then utilized in step 251 to provide the machine data to an automated milling machine to reproduce the original object using the data of the scan. In step 252 the reproduction is then scaled to produce a reproduction equal to the original object; likewise, the reproduction may be scaled to any desired size without introducing any distortion. In step 253 the automated machine then carries out the cutting or milling to reproduce the object.

Figure 15:
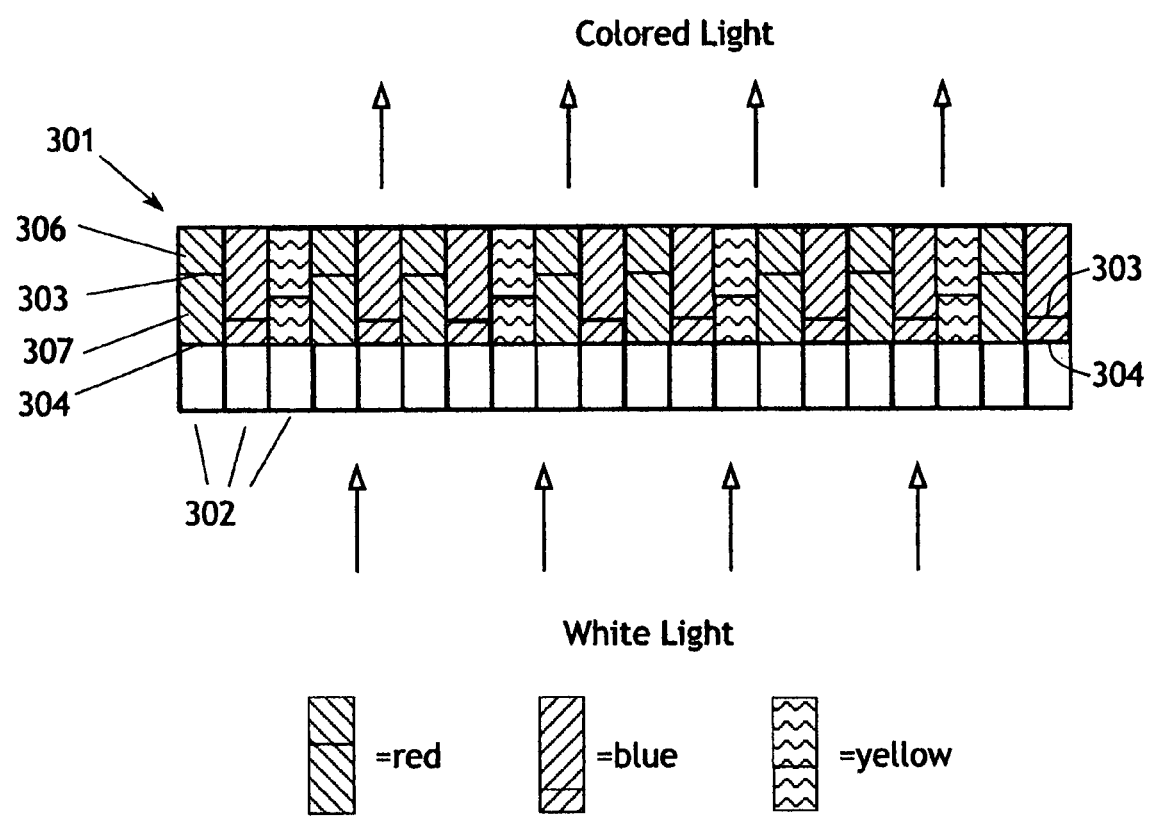
FIG. 15 is schematic layout of an interference filter that projects stripes of different colors toward an object undergoing dimensional mapping in accordance with this invention.

FIG. 15 depicts one embodiment of an arrangement for projecting colored stripes onto the object undergoing dimensional mapping. A constructive interference filter 301 is disposed to receive incident white light (or multi-wavelength light), processing the incident light, and emitting stripes of spectral colored light. The filter 301 is comprised of a plurality of sections 302 arrayed laterally in abutting arrangement.

Each section includes two half-reflective metal surfaces 303 and 304 embedded between two glass segments 306 and 307. A substantial fraction of the incident white light undergoes multiple reflections back and forth between the surfaces 303 and 304. Only light of a particular wavelength (a particular color) undergoes constructive interference, and the spacing of surfaces 303 and 304 of each section determines its respective wavelength. Note that in FIG. 15 the sections producing blue light have the smallest spacing of surfaces 303 and 304, while section producing red light have the greatest spacing.

The sections may be divided into subsets of identical output wavelengths, and the subsets distributed in an orderly pattern, whereby colored stripes of known spacing and repetition are projected toward the target object. The wavelength of each section is given by the following relationship:

$$d = \frac{\lambda}{2n\cos\beta}$$
$$= \lambda/2n \text{ (assuming normal incidence or } \beta = 0\text{)}$$

where
n=index of refraction of the glass;
λ=wavelength of light;
d=spacing of reflective surfaces.

A significant advantage of this embodiment is that the construction primarily of glass materials imparts a considerable heat-resistant characteristic to the filter 301, enabling the use of high power projection sources. Furthermore, the color wavelengths of interference filter 301 may be selected to match the color sensitivities of the camera image sensor(s) of cameras 10 or 11 described previously, whereby the optical resolution and the dimensional accuracy of the invention may be maximized.

The foregoing description of the preferred embodiments of the invention has been presented for purposes of illustration and description. It is not intended to be exhaustive or to limit the invention to the precise form disclosed, and many modifications and variations are possible in light of the above teaching without deviating from the spirit and the scope of the invention. The embodiment described is selected to best explain the principles of the invention and its practical application to thereby enable others skilled in the art to best utilize the invention in various embodiments and with various modifications as suited to the particular purpose contemplated. It is intended that the scope of the invention be defined by the claims appended hereto.

The invention claimed is:

1. A method for creating a three dimensional map of the surface of an object, including the step of: selectively projecting a sequence of patterns on at least one portion of the surface of the object, including an initial flash pattern and at least one secondary pattern; digitally capturing the image of said sequence of patterns on the object; calculating the distance of each incremental portion of the image to the object, and storing the distance data to comprise the three dimensional map; rendering a three dimensional image of said at least one portion of the surface of the object using the data from the three dimensional map:

further including the step of establishing a fiducial distance from said image to said object and scaling said distance data according to said fiducial distance, wherein said step of establishing the fiducial distance includes scanning an object of known dimensions from a plurality of different views.

2. The method of claim 1 wherein said initial flash pattern comprises a plurality of closely spaced stripes of different colors.

3. The method of claim 2 wherein the pattern of colored lines is provided by a pattern or film in a projector.

4. The method of claim 2, wherein said flash pattern is formed by an interference filter.

5. The method of claim 4, wherein said interference filter includes a plurality of sections in closely spaced lateral array, each section including partially reflective surfaces that establish an interference effect unique that generates a wavelength unique to each of said sections.

6. The method of claim 5, wherein said partially reflective surfaces are spaced along the optical transmission axis of said interference filter, said spacing determining said unique wavelength.

7. The method of claim 5, further including the step of providing a plurality of subsets of said sections, each subset generating substantially the same wavelength, said subsets being distributed in an orderly pattern in said interference filter, whereby colored stripes of known spacing, color, and repetition are projected toward the object.

8. The method of claim 2, wherein the color wavelengths of said color stripes are matched to the maximum color sensitivities of the device that carries out said step of digitally capturing the image.

9. The method of claim 2 wherein the pattern of colored stripes is provided by a digital programmable projector.

10. The method of claim 1, wherein said initial flash pattern is used to calculate a complete initial three dimensional map of said one portion of said object, and said at least one secondary pattern is used to detect changes from said initial three dimensional map and to update said initial three dimensional map.

11. The method of claim 10, wherein said initial flash pattern comprises a plurality of closely spaced colored stripes.

12. The method of claim 11, wherein said at least one secondary pattern comprises a plurality of closely spaced black and white stripes.

13. The method of claim 1, further including the step of using as said object a wound to an animal or human body, and treating and monitoring said wound based on the three-dimensional map thereof.

14. The method of claim 10, wherein said secondary pattern is reiterated rapidly, whereby said updated three dimensional map comprises a real-time record of the motion of said portion of said object.

15. The method of claim 14, further including the step of displaying the motion of said object as a three dimensional movie.

16. The method of claim 15, further including the step of acquiring the data for said three dimensional movie in real time, and displaying said three dimensional movie in real time.

17. The method of claim 1 wherein said object is a human body, and said three dimensional map is applied to the study of a human body breathing.

18. The method of claim 1 wherein said object is a mechanical structure, and said three dimensional map is applied to studying how the strain of an object changes in time.

19. The method of claim 1 wherein said object is a human body, and said three dimensional map is applied to the study of the human body walking motion.

20. The method of claim 1 used for machine vision of rapidly moving objects by maintaining a constant pattern while the objects move through the constant pattern.

21. The method of claim 1 used to produce 3-d images for inspection either during or after a manufacturing process.

22. The method of claim 1 used to provide computer data to develop computer generated manufacturing procedures (CAM), or computer aided design (CAD) procedures.

23. The method of claim 1 used with models of objects to provide enlarged or expanded data to manufacture full scale objects.

24. The method of claim 1 used to inspect railroad rails and/or roads for maintenance and repair determinations.

25. The method of claim 1 used to measure dimensions of human and/or animals to determine effects of diets or of medical treatments.

26. The method of claim 1 used to measure the dimension of injured portions of bodies to provide the information needed to construct prosthetic parts or devices.

27. The method of claim 1 used to obtain dental information to aid in providing dental devices or prosthetics.

28. The method of claim 1 used to obtain building structures or room dimensions, and/or configurations to aid in architecture for building design and modifications.

* * * * *